United States Patent
Zhang et al.

(10) Patent No.: US 10,014,167 B2
(45) Date of Patent: Jul. 3, 2018

(54) ION OPTICAL APPARATUS AND MASS SPECTROMETER

(71) Applicant: SHIMADZU CORPORATION, Nakagyo-ku, Kyoto (JP)

(72) Inventors: Xiaoqiang Zhang, Shanghai (CN); Qiao Jin, Shanghai (CN); Wenjian Sun, Shanghai (CN)

(73) Assignee: SHIMADZU CORPORATION, Nakagyo-Ku, Kyoto (JP)

( * ) Notice: Subject to any disclaimer, the term of this patent is extended or adjusted under 35 U.S.C. 154(b) by 0 days.

(21) Appl. No.: 15/503,523

(22) PCT Filed: Sep. 2, 2015

(86) PCT No.: PCT/CN2015/088841
§ 371 (c)(1),
(2) Date: Feb. 13, 2017

(87) PCT Pub. No.: WO2016/034125
PCT Pub. Date: Mar. 10, 2016

(65) Prior Publication Data
US 2017/0236698 A1    Aug. 17, 2017

(30) Foreign Application Priority Data
Sep. 4, 2014    (CN) .......................... 2014 1 0448494

(51) Int. Cl.
*H01J 49/06*    (2006.01)
*H01J 49/26*    (2006.01)
(Continued)

(52) U.S. Cl.
CPC .......... *H01J 49/062* (2013.01); *G01N 27/622* (2013.01); *H01J 49/42* (2013.01)

(58) Field of Classification Search
USPC ....... 250/281–283, 288, 290, 293, 294, 296, 250/526
See application file for complete search history.

(56) References Cited

U.S. PATENT DOCUMENTS 6,051,832 A * 4/2000 Bradshaw ............ G01N 27/622
                                                        250/281
6,157,031 A * 12/2000 Prestage ............. H01J 49/0018
                                                        250/290
(Continued)

FOREIGN PATENT DOCUMENTS

CN    1585081 A    2/2005
CN    101022076 A    8/2007
(Continued)

OTHER PUBLICATIONS

Office Action issued by the Japan Patent Office (JPO) dated Jan. 30, 2018 for Application No. JP2017-502983, Japan.
(Continued)

*Primary Examiner* — Bernard Souw
(74) *Attorney, Agent, or Firm* — Tim Tingkang Xia, Esq.; Locke Lord LLP

(57) ABSTRACT

An ion optical apparatus and a mass spectrometer are provided. The ion optical apparatus includes at least one planar insulating substrate which is covered with metal patterns to form an electrode array including a plurality of cell electrodes, wherein each of the cell electrodes is arrayed according to a first direction to form a geometric pattern distribution of the electrode array, wherein cell electrodes are applied with radio frequency (RF) voltages having different phases to confine ions, a direct current (DC) voltage gradient is applied along at least part of the cell electrodes in the electrode array to drive ions to move in the first direction along the electrode array, and a corresponding electric field distribution is formed by the geometric pattern (Continued)

distribution to drive ions to move in a second direction substantially orthogonal to the first direction, thereby realizing ion deflection, focusing or defocusing.

17 Claims, 13 Drawing Sheets

(51) Int. Cl.
*G01N 27/62* (2006.01)
*H01J 49/42* (2006.01)

(56) References Cited

U.S. PATENT DOCUMENTS

| | | | | |
|---|---|---|---|---|
| 6,972,406 | B2* | 12/2005 | Syms | H01J 49/0018 |
| | | | | 250/281 |
| 7,498,570 | B2* | 3/2009 | Boyle | G01N 27/624 |
| | | | | 250/281 |
| 2009/0026361 | A1* | 1/2009 | Syms | H01J 3/14 |
| | | | | 250/281 |
| 2011/0180702 | A1* | 7/2011 | Flory | H01J 49/406 |
| | | | | 250/282 |
| 2014/0084156 | A1 | 3/2014 | Ristroph et al. | |
| 2014/0263999 | A1* | 9/2014 | Ramsey | H01J 49/0022 |
| | | | | 250/281 |

FOREIGN PATENT DOCUMENTS

| | | |
|---|---|---|
| CN | 101416271 A | 4/2009 |
| JP | 2006332003 A | 12/2006 |
| JP | 2016514896 A | 5/2016 |
| WO | 2013098612 A1 | 7/2013 |

OTHER PUBLICATIONS

International Search Report (ISR) issued by the State Intellectual Property Office of the Peoples Republic of China dated Nov. 24, 2015 for PCT/CN2015/088841, China.

* cited by examiner

ION OPTICAL APPARATUS AND MASS SPECTROMETER

FIELD OF THE INVENTION

The invention relates to the technical field of mass spectrographic analysis, and particularly to an ion optical apparatus for a mass spectrometer and the mass spectrometer.

BACKGROUND OF THE INVENTION

An ion optical apparatus is mainly used as an ion transmission or guiding device in a mass spectrometer so as to introduce ions generated from an ion source into a mass analyzer. An ion optical apparatus in the form of an electrode array, e.g., those described in U.S. Pat. Nos. 6,107,628 and 8,581,181 as well as Chinese Patent CN201210203634, etc., has been widely used in the industry due to its flexibility in design and function.

Currently, a process for fabricating an electrode array mainly comprises the steps of directly fabricating a discrete pure metal electrode device, and then positioning and fixing it by a tooling fixture. The fabrication by pure metal electrodes has the following advantages: firstly, the machining precision can be very high and can easily meet the requirements of an ion optical device; and secondly, the device has no insulating portion itself, thus avoiding charge accumulation. However, such process is usually very complex, time-consuming and relatively expensive due to a larger number of electrode arrays; and a very large capacitance will be introduced by the electrode arrays, so a power supply with a very large power output will be required. To reduce the fabrication cost and capacitance, a better approach is to use a stacked printed circuit board (PCB), wherein edges of the PCB are coated with a metal coating as an electrode, while other pieces of PCB which are not covered with the metal coating serves as the insulting layers, and then multiple PCBs are stacked to form an electrode array. Although the PCB process is mature, tooling is required for positioning in the multiple-piece stacking process, which involves a relatively complex procedure. In addition to the edges of the PCB, the surface of the PCB can also be plated with an electrode to form an ion optical device, for example, the PCB process is used to fabricate the flight tube, the acceleration electrodes, the mirror electrodes, etc. of a time-of-flight mass spectrometer in U.S. Pat. No. 6,316,768, and the PCB process is also used to fabricate a planar linear ion trap in U.S. Pat. No. 7,498,569.

In addition, in recent years, with the rapid development of a micro/nanofabrication technology and a micro-electromechanical system (MEMS), many people have begun to apply them to the fabrication of ion optical devices, especially ion traps. Although the nanofabrication technology emphasizes a three-dimensional structure compared with a PCB technology in a conventional IC process, a planar metal coating on the surface of an insulating layer is mainly used as an electrode in the current ion optical devices (see, for example, U.S. Pat. Nos. 7,217,922, 7,402,799, 8,213,118 and 8,299,443).

Although there have been numerous examples of the mature PCB process and the rapidly-developing MEMS process applied to ion optical devices, a cell electrode of an electrode array itself has so far been only used as a voltage applying point or surface, so the cell electrode takes the shape of a simple geometric configuration such as a point, a line or a rectangle. Accordingly, numerous cell electrodes and a matching power supply system are needed to obtain a certain complex potential distribution, or the three-dimensional electrodes with very complex structures can only be used to form a desired corresponding spatial electric field distribution.

SUMMARY OF THE INVENTION

In view of the above disadvantages of the prior art, an object of the invention is to provide an ion optical apparatus to be used in a mass spectrometer so as to solve technical problems in the prior art that a complex potential distribution is relatively difficult to realize in an electrode array or a complex structure and difficult processing are required even if that can be realized, etc.

To achieve the above object and other related objects, the invention provides an ion optical apparatus comprising at least one planar insulating substrate which is covered with metal patterns to form an electrode array, wherein the electrode array comprises a plurality of cell electrodes, the plurality of cell electrodes is arrayed according to a predefined ion guiding direction to form a geometric pattern distribution of the electrode array, and the predefined ion guiding direction is defined as a first direction, wherein each of adjacent cell electrodes is applied with RF voltages having different phases to confine ions, a DC voltage gradient is also applied along at least part of the cell electrodes in the electrode array to drive ions to move in the first direction, and a corresponding electric field distribution is formed by the geometric pattern distribution of the electrode array and drives ions to move in a second direction substantially orthogonal to the first direction, thereby realizing ion deflection, focusing or defocusing. In implementation, cell electrodes having various planar geometries may be printed by a PCB or MEMS process, which provides the advantages of low cost, high precision, high flexibility, etc.

Optionally, the geometry of the at least part of the cell electrodes in the electrode array is a broken line or a curve to form an electric field distribution corresponding to the geometric pattern distribution of the electrode array.

Optionally, the ion optical apparatus comprises at least a pair of the planar insulating substrates which are arranged such that respective cell electrodes are opposite to each other in the second direction to form an electric field distribution between paired planar insulating substrates, thereby causing the deflection, focusing or defocusing of the ions in the second direction.

Optionally, the ion optical apparatus comprises at least two said planar insulating substrates having a common edge formed by edge joining or at least three said planar insulating substrates having a common corner formed by corner joining, wherein said cell electrodes having gradually reduced sizes are distributed on the planar insulating substrates in a direction where the cell electrodes come closer to a point on the common edge or the common corner, such that the ions are focused towards the point on the common edge or the common corner.

Optionally, the ion optical apparatus comprises at least four said planar insulating substrates which are joined in a surrounding manner to form an ion guiding chamber, arrays of ring electrodes being formed in a spaced manner on an inner surface of the ion guiding chamber in the first direction, wherein at least part of the ring electrodes on at least two said planar insulating substrates are respectively isolated into two segments by an oblique insulating strip to form a first cell electrode and a second cell electrode such that the first cell electrode and the second cell electrode gradually change in length in the predefined ion guiding direction, and a DC voltage bias is applied between the first cell electrode and the second cell electrode so as to drive the ions to be focused while deflecting in the second direction.

Optionally, the ion optical apparatus comprises at least four said planar insulating substrates which are joined in a surrounding manner to form an ion guiding chamber, wherein a plurality of cell electrodes is arranged in a spaced manner on each surface inside the ion guiding chamber in the first direction and the second direction, and different DC voltages are applied along at least part of the cell electrodes to form a corresponding electric field distribution so as to drive the ions to deflect, focus or defocus in the second direction.

Optionally, the DC driving electric field can be replaced by an RF electric field which generates pseudo potential barriers having different intensities in the second direction to drive the ions to deflect, focus or defocus.

Optionally, parameters involving the geometric pattern distribution of the electrode array include one of the length, radius and curvature of the cell electrodes in the electrode array and an included angle relative to the first direction, or one or more combinations thereof.

Optionally, the parameters gradually change in the first direction to form a corresponding electric field distribution.

Optionally, the planar insulating substrate is in a rectangular shape.

Optionally, the planar insulating substrate is a substrate of a printed circuit board and the metal coating is a printed circuit.

Optionally, at least part of electronic components for forming the DC or RF electric field are located on the printed circuit board.

Optionally, a portion of the planar insulating substrate that is not covered with the metal patterns is provided with a cut slot or covered with a coating having a high resistance value.

Optionally, the planar insulating substrate and the metal patterns are obtained by a micro/nanofabrication process.

To achieve the above object and other related objects, the invention provides a mass spectrometer comprising the ion optical apparatus for ion guiding.

Optionally, the mass spectrometer comprises a mass analyzer used in combination with the ion optical apparatus.

Optionally, the mass spectrometer comprises an ion mobility analyzer used in combination with the ion optical apparatus.

As described above, the invention provides an ion optical apparatus and a mass spectrometer. The ion optical apparatus comprises at least one planar insulating substrate which is covered with metal patterns to form an electrode array comprising a plurality of cell electrodes, wherein the plurality of cell electrodes is arrayed according to a predefined ion guiding direction (i.e., a first direction) to form a geometric pattern distribution of the electrode array, each of adjacent cell electrodes is applied with RF voltages having different phases to confine ions, a DC voltage gradient is also applied along at least part of the cell electrodes in the electrode array to drive ions to move in the first direction along the electrode array, and a corresponding electric field distribution is formed by the geometric pattern distribution and drives ions to move in a second direction substantially orthogonal to the first direction, thereby realizing ion deflection, focusing or defocusing. In the invention, various desired spatial electric field distributions are formed by the geometric structure and distribution of the planar electrodes. In one preferred embodiment, ions can be effectively focused within a broader pressure range by only two flat PCBs, and in another preferred embodiment, ions can be transmitted in an off-axis manner and focused to reduce neutral noise. In implementation, cell electrodes having various planar geometries are printed by a PCB or MEMS process, which provides the advantages of low cost, high precision, high flexibility, etc.

BRIEF DESCRIPTION OF THE DRAWINGS

FIG. 1b shows an ion trajectory view obtained by computer simulation according to the embodiment of FIG. 1a;

FIG. 2b shows a partial schematic structural view of FIG. 2a;

FIG. 2c shows a sectional schematic structural view of FIG. 2a;

DETAILED DESCRIPTION OF THE INVENTION

The embodiments of the invention will be described hereinafter through specific particular examples, and those skilled in the art can easily understand other advantages and effects of the invention through the disclosed contents in the specification. The invention may also be implemented or applied through other different particular embodiments, and various modifications or changes may also be made to various details in the specification on the basis of different opinions and applications without departing from the spirit of the invention. It should be noted that the embodiments in the present application and the features in the embodiments may be combined with each other if there is no confliction.

One of improvements in the ion optical apparatus of the invention is that at least one planar insulating substrate is covered with metal patterns to form an electrode array, and a desired electric field distribution is formed by a geometric pattern distribution of the electrode array to drive ions to move towards a desired direction or position, and a plurality of insulating substrates printed with matching metal patterns can be combined to achieve the electric field distribution effects of an existing three-dimensional electrode. In one embodiment, the covering the planar insulating substrate with metal patterns may be realized by a PCB printing manner and also by a micro/nanofabrication process (MEMS).

Figure 1A:
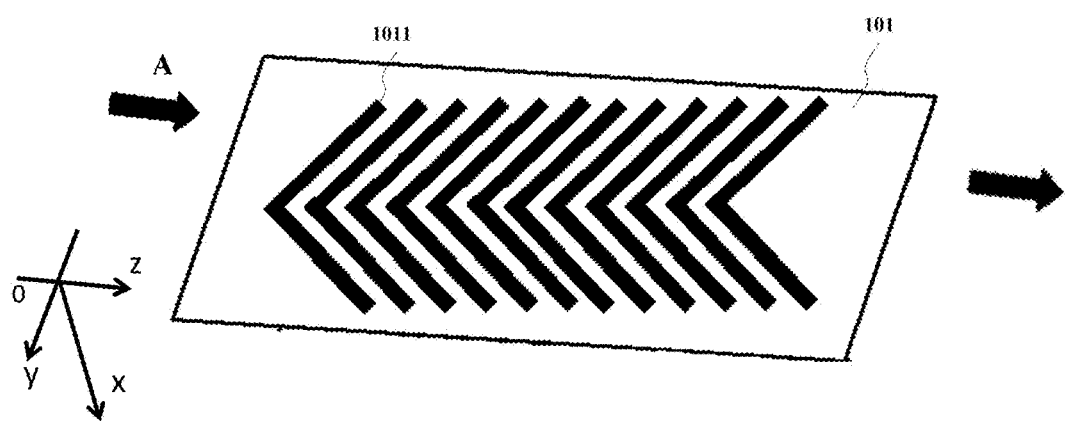
FIG. 1a shows a schematic structural view of an embodiment of an ion optical apparatus of the invention.

With reference to FIG. 1a, in the embodiment, the ion optical apparatus comprises one planar insulating substrate 101 which is covered with metal patterns to form an electrode array, wherein the electrode array comprises a plurality of cell electrodes 1011, the plurality of cell electrodes 1011 is arrayed to form a geometric pattern distribution of the electrode array, the planar insulating substrate 101 may be rectangular, square or the like, and the geometry of at least part of the cell electrodes 1011 in the electrode array thereon may be in a shape of a broken line as shown. Further optionally, the broken line is centrosymmetric, i.e., two broken line segments are left-right symmetric relative to a central line where a connection point is located. Moreover, the ion optical apparatus can also supply RF voltages having different phases to each of adjacent and mutually insulated cell electrodes 1011 by a power source to confine ions, in order to confine ions and prevent ions from wall collision. In one embodiment, said different phases mean that RF voltages on adjacent cell electrodes may have an equal amplitude, but opposite phases. Moreover, a DC voltage gradient is also applied along at least part of the cell electrodes 1011 in the electrode array by a power source, for example, the amplitude gradually changes from low to high or from high to low. In the embodiment, i.e., for example, the amplitude of a DC voltage applied to each of the cell electrodes 1011 in a positive direction of a z axis decreases, and when ions are injected into an electric field of the electrode array according to the direction of an arrow A as shown, the ions will move from high-potential electrodes to low-potential electrodes until exiting from the other side, thereby realizing ion guiding. However, each ion injected into the electric field formed by the electrode array will move in a predefined ion guiding direction along the electrode array, wherein the predefined ion guiding direction will be defined as a first direction herein and hereinafter, and the predefined ion guiding direction, i.e., a predefined direction of an ion guiding axis, will be a central axial direction of a centrosymmetric ion guiding chamber (abbreviated as an axial direction and shown as the direction of the z axis) if in the chamber, and may be an ion guiding direction along the electrode array outside said one planar insulating substrate 101 in the embodiment, and a substantially orthogonal direction of the axial direction can be defined as a radial direction. Although the axial direction and the radial direction described in the embodiment are defined differently from those of three-dimensional shapes such as cylinders and cubes, it could be understood by those skilled in the art according to the contents of the description and the drawings. After the electrode array comprising the cell electrodes 1011 is charged with a DC voltage, a corresponding electric field distribution may be formed by its geometric pattern distribution to drive each of the ions to deflect, focus or defocus in a second direction substantially orthogonal to the first direction. An approach combining deflection with focusing is provided in the embodiment, but, of course, an implementation approach of defocusing can also be deduced therefrom, which will be described hereinafter.

Optionally, all the above cell electrodes 1011 may have the same structure and spacing, and are focused by a DC electric field while an RF electric field is only used to confine ions and prevent ions from hitting a wall and will not cause RF trapping, thereby avoiding discrimination to low-mass ions. However, in a traditional scheme, because of a very small electrode aperture or a great electrode spacing at an exit, an RF voltage will form a quadrupole ion trap to trap low-mass ions which hence cannot be effectively transmitted to the next stage, but the design of the invention avoids this problem.

Figure 1B:
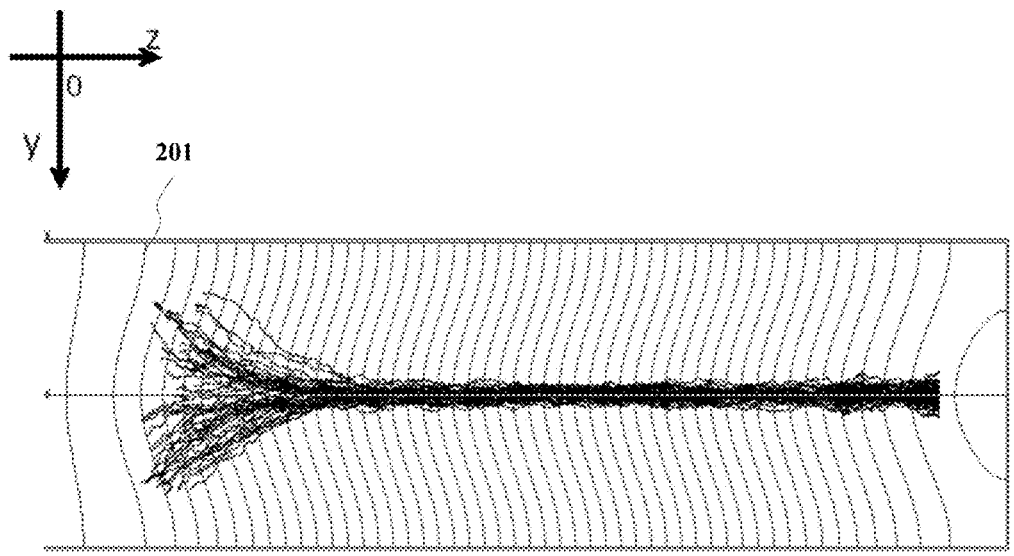

Together with reference to FIG. 1b, an ion trajectory simulation result of the embodiment in FIG. 1a is shown, from which it could be understood that the electric field distribution, i.e., a distribution of individual electric field lines 201 as shown, is similar to the geometric pattern distribution of the electrode array comprising the above cell electrodes, and is a focusing electric field pointing to both a positive direction of a z axis and the origin of a y axis. Each of the ions moves in the y axis to be focused towards a central line as shown (i.e., a position where the z axis is located) under the action of the electric field distribution immediately after entering the electric field according to the positive direction of the z axis as shown, wherein ions which are not located on the central line deflect in the y axis and move to the central line to be focused.

Figure 1C:
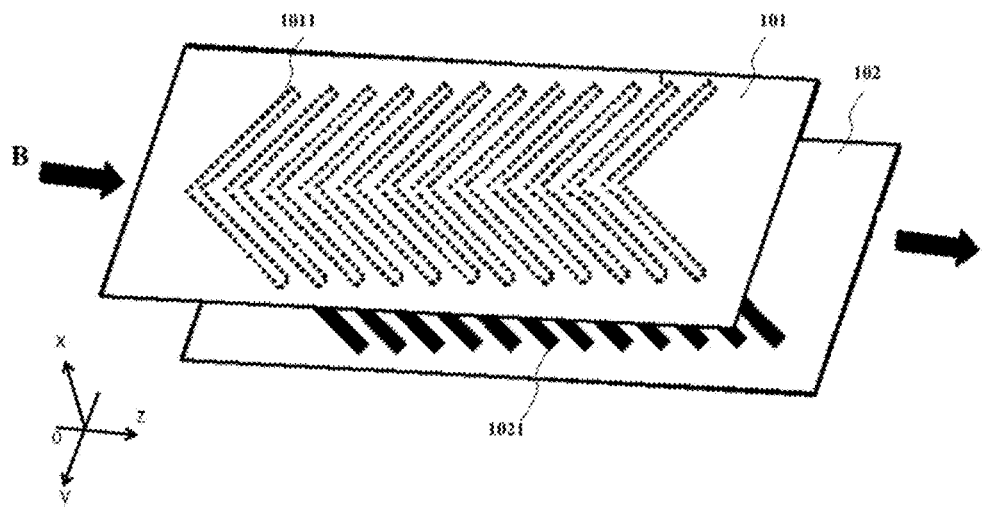
FIG. 1c shows a schematic structural view of an embodiment of the ion optical apparatus of the invention for implementing ion focusing.

With reference to FIG. 1c, in the embodiment, a pair of identical upper and lower insulating substrates 101 and 102 are used, and can be arranged in parallel to each other and are arranged such that their respective cell electrodes 1011 and 1021 are opposite to each other in a second direction, i.e., an x direction as shown. Compared with the previous embodiment, the embodiment has the advantage that ions pass between the upper and lower substrates, which may be more favorable for confining ions, but in the structure in FIG. 1a, ions need to be closer to the insulating substrate, otherwise ions probably will escape from an electric field under the external action. In the embodiment, in terms of voltage application, a DC voltage bias may be applied between upper and lower electrode arrays (i.e., a DC voltage bias is applied between paired opposite cell electrodes 1011 and 1021) such that ion beams deviate to one of the insulating substrates, thus focusing may also be realized in the x direction.

Indeed, if defocusing needs to be realized, ion beams can be reversely injected at an ion exit in the above embodiment, and a DC potential gradient is reversely arranged along the individual cell electrodes 1011, for example, the amplitude of the voltage in the positive direction of the z axis decreases in the previous embodiment while the amplitude of the voltage in the positive direction of the z axis increases, i.e., ion guiding is implemented in a direction opposite to that of the above embodiment, thus ion defocusing can be realized.

Moreover, although the cell electrodes 1011 shown take the shape of a broken line in the above embodiment, their shape may also be an arc or each cell electrode may consist of two discrete linear electrodes in other embodiments, which can also realize a similar electric field distribution.

Figure 2A:
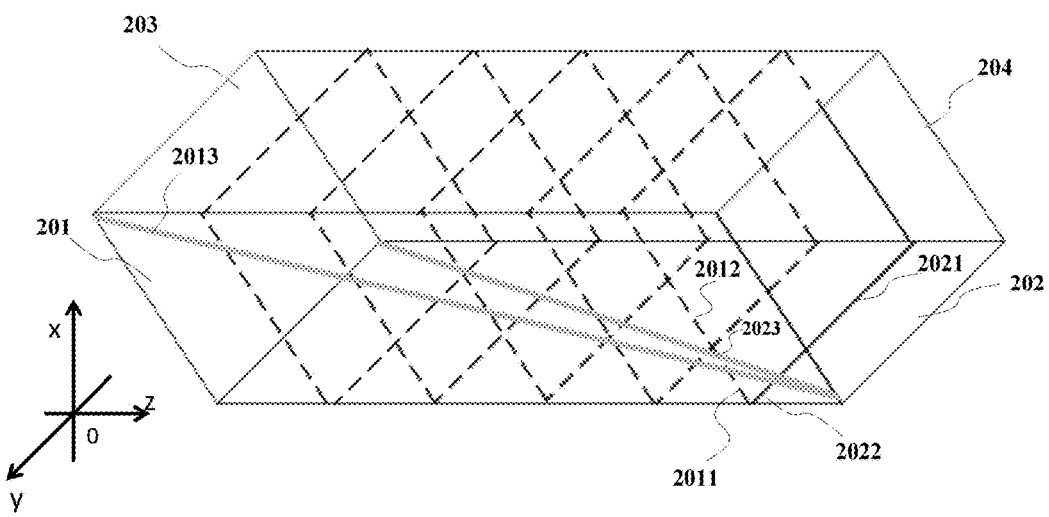
FIG. 2a shows a schematic structural view of an embodiment of the ion optical apparatus of the invention for implementing ion focusing.
Figure 2B:
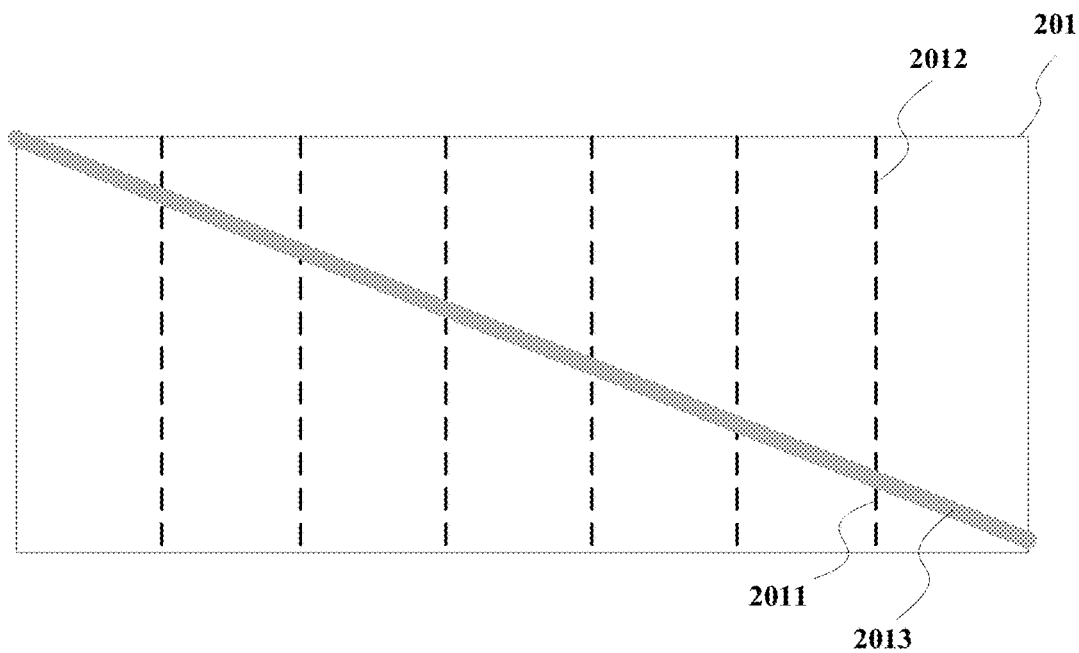
Figure 2C:
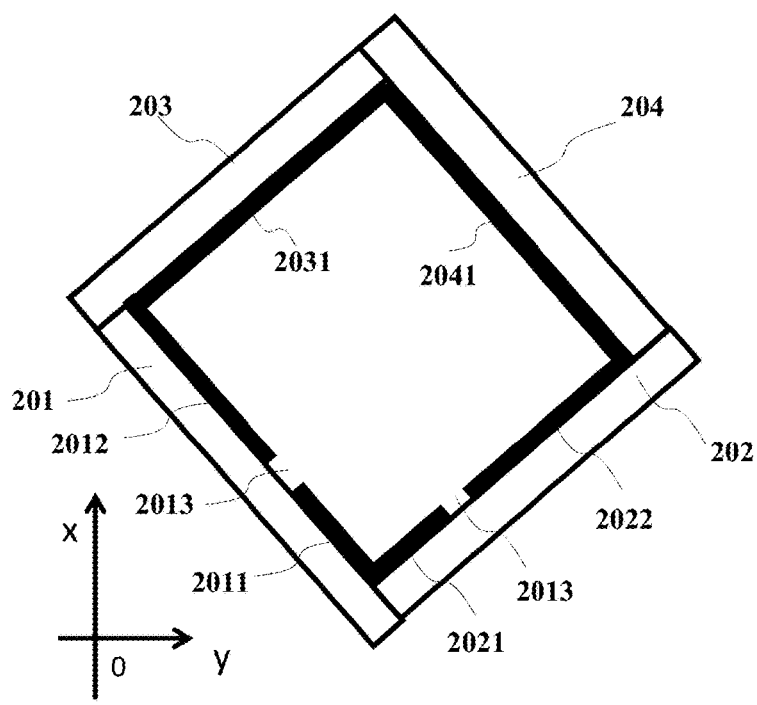

Another example is taken to illustrate how to form a focusing electric field in a radial direction substantially orthogonal to a predefined ion guiding direction (i.e., an axial direction) by virtue of a gradual change in the geometric dimension of discrete electrodes. As shown in FIGS. 2a and 2b, at least four said planar insulating substrates 201, 202, 203 and 204 can be used to be joined in a surrounding manner to form an ion guiding chamber, wherein FIG. 2b simply illustrates the planar insulating substrate 201 (having a structure similar to that of the planar insulating substrate 202); and a first direction (i.e., an axial direction) is set as a positive direction of a z axis as shown. Together with reference to FIG. 2c, a sectional view of FIG. 2a in a z axis is shown, wherein the entire ion guiding chamber is arranged as a quadrangle having a diagonal line consistent with an x axis when viewed from the direction of the z axis, and electrode arrays comprising a plurality of ring electrodes are arranged in a spaced manner on an inner surface of the ion guiding chamber in the z axis (i.e., the axial direction). In the embodiment, because four rectangular planar insulating substrates are used to form a cubic ion guiding chamber in a surrounding manner, the ring electrodes that can be formed are in square shape, and the shape is certainly only illustrative rather than limiting. Together with reference to FIG. 2b, two lower planar insulating substrates 201 and 202 with oblique insulating strips 2013 and 2023 are shown. With reference to FIG. 2c, the ring electrodes on the two lower planar insulating substrates 201 and 202 are respectively isolated into two segments by the oblique insulating strips, and there is an angle of e.g., 0-90°, preferably 15-60° between the oblique insulating strip and the axial direction, such that individual segments at both sides of the oblique insulating strips 2013 and 2023 gradually change in length in the predefined ion guiding direction, i.e., the first direction. For the convenience of description, the oblique insulating strip 2013 on the planar insulating substrate 201 isolates each of the ring electrodes into a lower electrode 2011 and an upper electrode 2012, and the oblique insulating strip 2023 on the planar insulating substrate 202 isolates each of the ring electrodes into a lower electrode 2021 and an upper electrode 2022, wherein the electrodes 2011 and 2021 are connected to form a first cell electrode, and the electrodes 2012, 2031, 2041 and 2022 are electrically connected to form a second cell electrode, thereby respectively forming a lower first electrode array and an upper second electrode array. In order to confine ions, RF voltages having the same amplitude and opposite phases are applied between adjacent electrodes in the axial direction, ions may be bounced off when coming too closer to the electrode arrays, the first electrode array and the second electrode array are respectively applied with DC voltages descending in the axial direction (i.e., the positive direction of the z axis as shown) to drive ions to move in the first direction, and a DC electric field can be applied between individual corresponding first cell electrodes and second cell electrodes isolated by at least part of the ring electrodes to provide a voltage bias, thereby forming a corresponding electric field distribution to drive ions in the ion guiding chamber to deflect, focus or defocus in the radial direction (i.e., a second direction) substantially orthogonal to the axial direction. Specifically, for example, if the DC voltages of the individual first cell electrodes in the first electrode array are greater than those of the lower second cell electrodes, ions will deflect towards a negative direction of the x axis under the action of an electric field, otherwise, ions will deflect towards a positive direction of the x axis. The planar insulating substrates 201 and 202 as well as the electrode segments 2011 and 2021 thereon are symmetric relative to the direction of the x axis. In one embodiment, the ion optical apparatus works at a typical pressure ranging from e.g., 1 torr to 30 torr.

Specifically, when ions from an upstream ion source enter the ion optical apparatus and move in the axial direction, the ions are transmitted in the positive direction of the z axis in the apparatus under the axial action of the above electric field, and the ions radially gradually deviate to the negative direction of the x axis due to a DC voltage bias between the first electrode array and the second electrode array, and because there is an included angle between the insulating strip and the axial direction, i.e., the electrode length of the electrode arrays gradually decreases in the axial direction, then the ions are radially gradually focused and then transmitted into a downstream mass analyzer or other analyzing apparatuses.

It should be noted that the implementation of an ion focusing function is provided in the embodiment, but those skilled in the art can fully perform a reverse operation according to the foregoing contents to achieve an ion defocusing function, for example, ions are reversely injected and a reversed DC voltage is applied, etc., which will not be described by way of example.

Figure 3A:
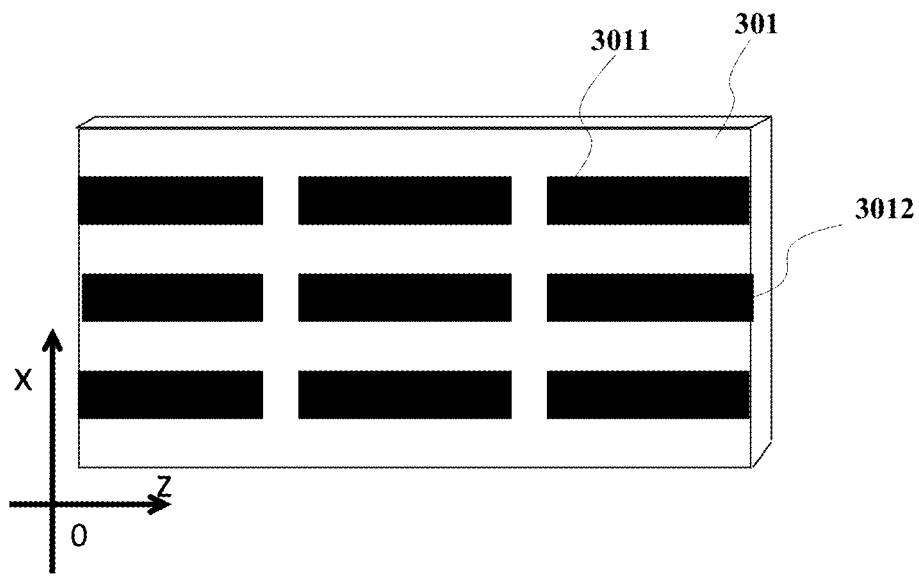
FIG. 3a shows a schematic structural view of an embodiment of the ion optical apparatus of the invention for implementing ion focusing.
Figure 3B:
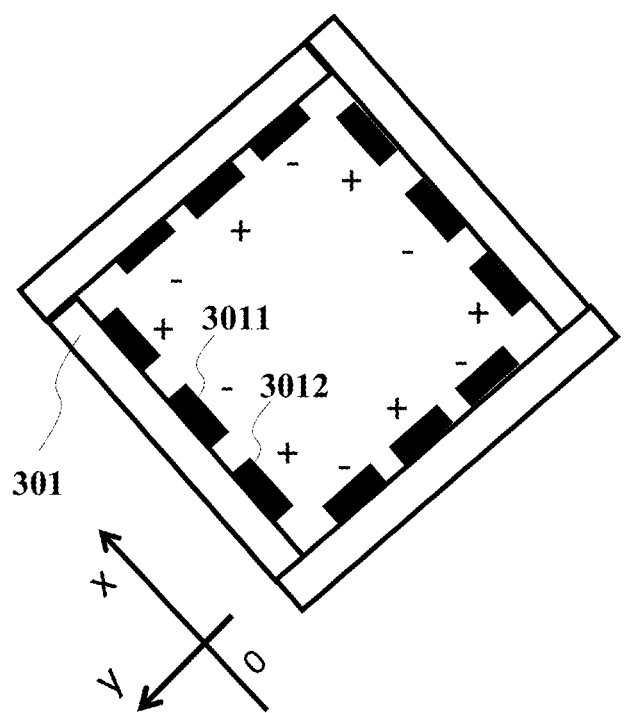
FIG. 3b shows a sectional schematic structural view of an embodiment of the ion optical apparatus of the invention for implementing ion focusing.

FIG. 3a shows a simple embodiment of the embodiment in FIG. 2b. This embodiment is different from the previous embodiment as follows: in the present embodiment, a plurality of cell electrodes is arranged in a spaced manner on each surface inside the ion guiding chamber (i.e., an inner surface of each planar insulating substrate 301) in the first direction (i.e., an axial direction, shown as the direction of a z axis) and its orthogonal direction, i.e., four planar insulating substrates 301 like those in FIG. 3a are joined in a surrounding manner to form the above ion guiding chamber, and optionally, cell electrodes on each of the planar insulating substrates 301 are synchronously arranged along the z axis, i.e., located on the same ring, similarly to the previous embodiment, except that the cell electrodes on the ring are separate and independent in the present embodiment, and a corresponding electric field distribution is formed to drive ions in the ion guiding chamber to deflect, focus or defocus radially while axially moving. Hereinafter, take the implementation of ion focusing as an example, as shown in FIG. 3a, in an xz plane, each planar insulating substrate 301 comprises at least two electrodes thereon, and optionally comprises three electrodes thereon as shown, wherein RF voltages applied between adjacent electrodes in a z direction may be exactly the same, and meanwhile, gradually decreasing DC voltages are applied to drive ions to be transmitted along the z axis. However, adjacent cell electrodes may have RF voltages having the same amplitude and opposite phases in an x direction such that an approximate twelve-stage field as shown in FIG. 3b can be formed, and meanwhile, different DC voltages are applied to compress and focus ion beams in x and y directions. For instance, if ion beams need to be compressed towards the origin of an xy plane (the direction of a z axis), a DC voltage bias can, for example, be applied between cell electrodes 3011 and 3012 such that ions move close to the cell electrode 3012. Compared to the embodiment in FIG. 2a, a transmission effect similar to that of a stacked electrode array can be obtained herein using a multi-stage field structure and a radial DC electric field, but fewer electrodes are used, thereby simplifying circuit connection. If different transmission effects need to be obtained, e.g., better radial focusing, rough mass separation or the like, a multi-stage field having lower stages (e.g., a four-stage field) can be obtained.

Figure 3C:
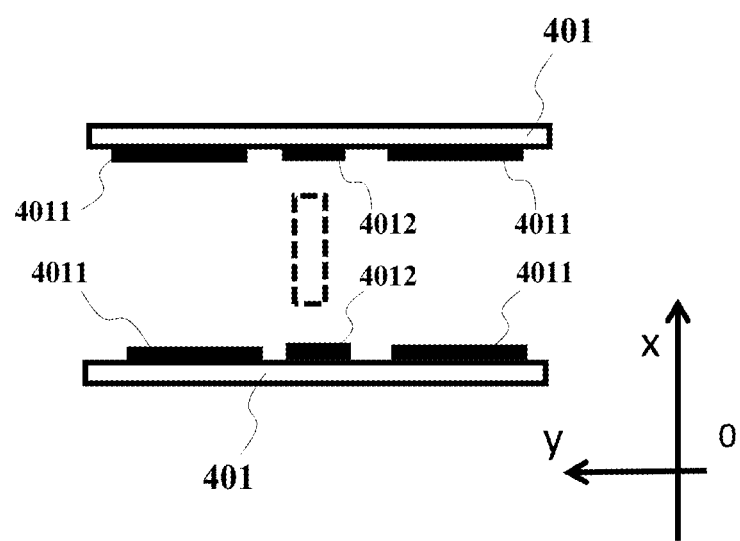
FIG. 3c shows a schematic structural view of an embodiment of the ion optical apparatus of the invention for implementing ion focusing.

In yet another embodiment, more simply, if compression or focusing is only required in one dimension, only two opposite planar insulating substrates 401 may be used, their sectional structure in an xy plane thereof can be as shown in FIG. 3c, cell electrodes 4011 at both sides are charged with the same DC voltage while cell electrodes 4012 have a DC voltage bias relative to the cell electrodes 4011 at both sides, and a DC electric field thus formed allows ions to be converged to the vicinity of the origin of a y axis, thereby forming an ion beam distribution that takes the shape of a long strip in an x axis, as shown by a dashed box in the Figure. Such distribution can be used for a preceding stage of an accelerating electrode of an orthogonal time-of-flight mass spectrometer. More simply, in one embodiment, the DC electric field is replaced by an RF electric field such that pseudo potential barriers having different intensities are generated by the RF electric field in a second direction to drive ions to deflect, focus or defocus. However, take the above embodiment as an example, the RF amplitude on the cell electrodes 4011 generally can be allowed to be greater than the amplitude on the cell electrodes 4012, then a stronger RF pseudo potential barrier will be generated in the vicinity of the cell electrodes 4012, ions will be converged to the vicinity of the origin in a y direction, and the ion focusing degree can be controlled by adjusting the field intensity ratio of RF. Such approach provides an circular ring electrode array or an elliptical ring array distributed in a z axis. In other words, a three-dimensional spatial electric field distribution is realized by an electrode structure of a flat board.

It should be noted that the implementation of an ion focusing function is provided in the above embodiment, but those skilled in the art can fully perform a reverse operation according to the foregoing contents to achieve an ion defocusing function, for example, ions are reversely injected and a reversed DC voltage is applied, etc., which will not be described by way of example.

Since an electric field implementation approach of a three-dimensional array is not limited to only the above-described embodiments, several embodiments will be used again hereinafter to illustrate other electric field distributions of a three-dimensional array comprising planar electrode structures on a plurality of the above insulating substrates.

Figure 4A:
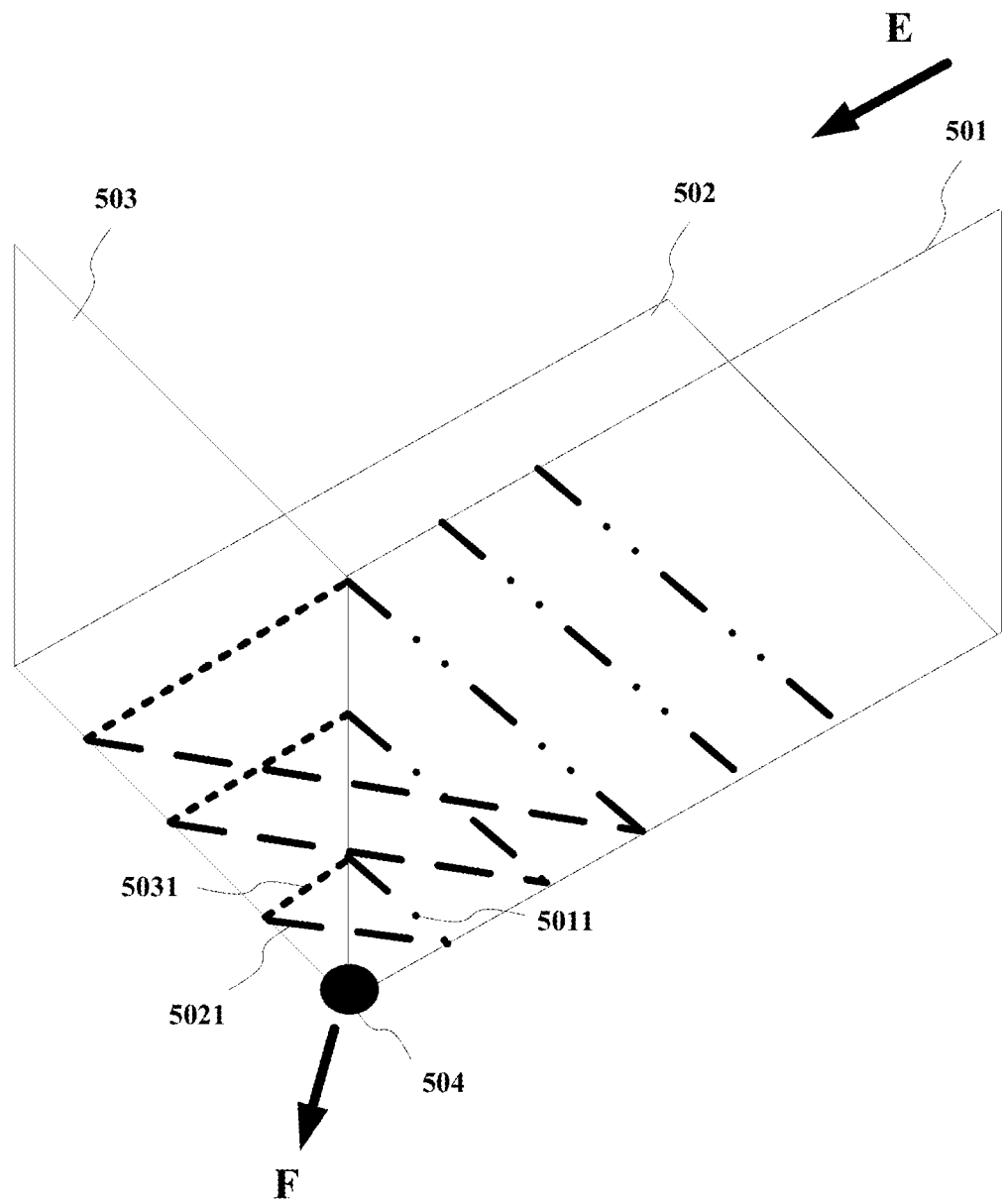
FIGS. 4a and 4b show schematic structural views of an embodiment of the ion optical apparatus of the invention for implementing ion focusing.
Figure 4B:
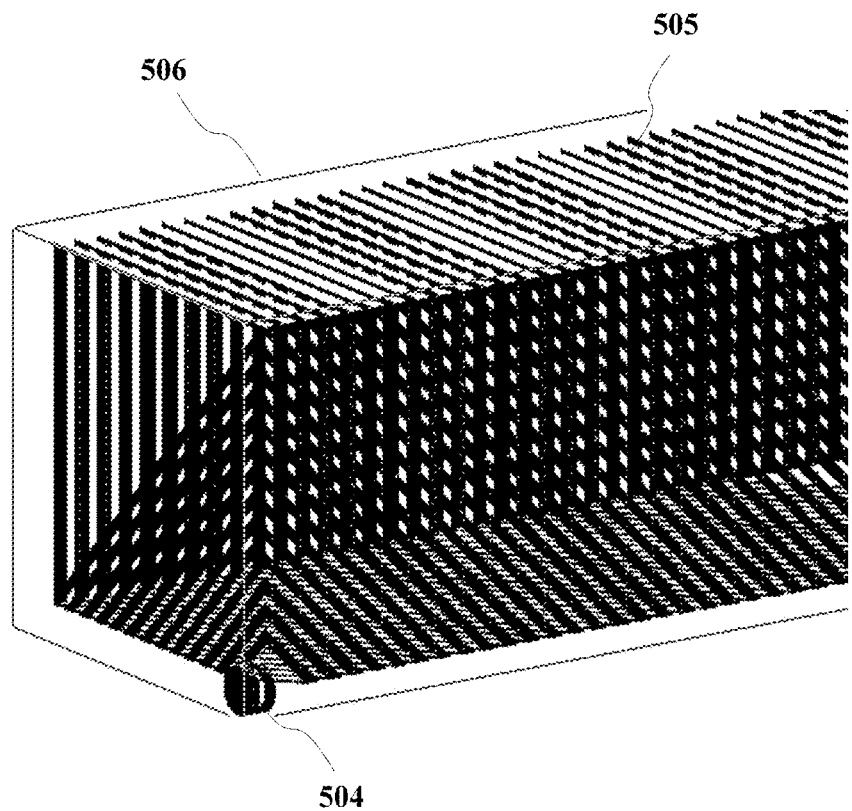
Figure 4C:
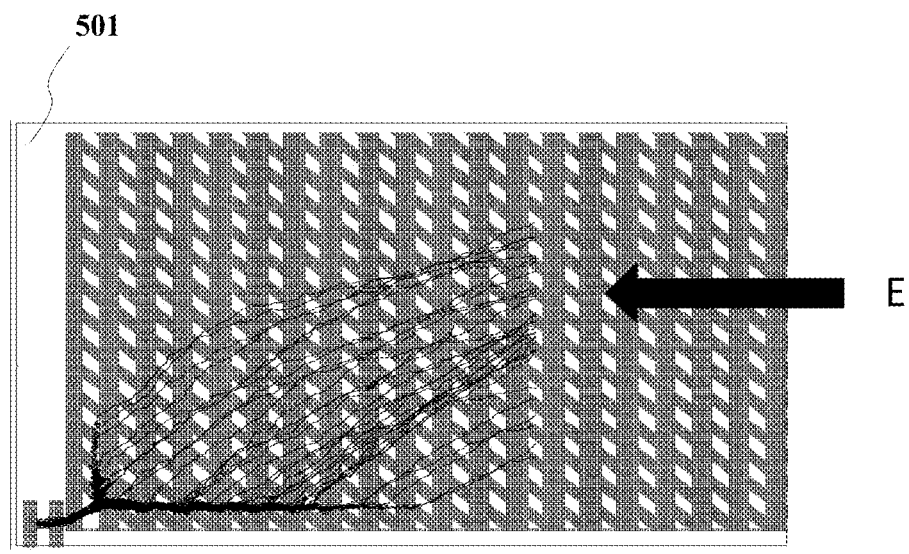
FIG. 4c shows an ion trajectory view obtained by computer simulation according to the embodiment of FIG. 4b.

As shown in FIGS. 4a to 4c, the ion optical apparatus may comprise three said planar insulating substrates having a common corner formed by corner joining, wherein cell electrodes having gradually reduced sizes are formed in a spaced manner on the three planar insulating substrates in a direction where the cell electrodes come closer to the common corner as a center, such that each of the ions is focused towards the common corner. Specifically, in one embodiment, as shown in FIG. 4a, three planar insulating substrates 501, 502 and 503 with better effects are used to form a common corner by corner joining, which is certainly only illustrative. According to the spirit of the invention, one planar insulating substrate is removed from the technical solution of the above embodiment, and similar effects can also be realized by only two planar insulating substrates which are joined by edges, wherein cell electrodes having gradually reduced sizes are distributed on the planar insulating substrates in a direction where the cell electrodes come closer to the common edge as a center, so the number of the planar insulating substrates is not limited to three as shown.

The three planar insulating substrates 501, 502 and 503 are combined with each other to form a solid-angular structure, strip metal electrodes are distributed on each substrate as cell electrodes 5011, 5021 and 5031, the strip electrodes take the shape of a straight line in the embodiment, but can also exhibit a broken line, a curve or the like as described above in other embodiments, and changes may be made by those skilled in the art in conjunction with the principle of the invention. The strip electrodes on each of the planar insulating substrates 501, 502 and 503 have the same spacing, and the strip electrodes on each of the planar insulating substrates 501, 502 and 503 which have the same distance from a common corner 504 are electrically connected. Because there are three planar insulating substrates in the embodiment, the connected strip electrodes form a triangular electrode (the triangular electrode formed of the electrically connected cell electrodes 5011, 5021 and 5031 can also be considered as an integral "cell electrode"), and the closer to the common corner 504, the smaller the area of the triangular electrode, i.e., the shorter the length of the individual cell electrodes 5011, 5021 and 5031. However, if there are two planar insulating substrates, they may be imagined as a broken-line electrode, and the closer to the common corner, the smaller the size. Optionally, in order that the apparatus can better confine ion beams, RF voltages having an equal amplitude and opposite phases can be applied between adjacent cell electrodes (e.g., adjacent cell electrodes 5011, adjacent cell electrodes 5021 or adjacent cell electrodes 5031) as described above, and ions may be bounced off when coming too closer to electrode arrays, and gradually decreasing DC voltages are applied to the electrode arrays, thereby forming a focusing electric field pointing to the common corner 504. Optionally, as shown in FIG. 4b, two planar insulating substrates 505 and 506 having stripe-spaced electrode arrays as shown can be added at a left side and a top side as shown in FIG. 4a, thereby forming a cuboid-shaped ion guiding chamber in a surrounding manner; and stripe electrodes on the planar insulating substrates 505 and 506 at the left side and the top side are axially parallel or perpendicular to the cuboid, and can be made to have the same spacing as stripe electrodes on other planes so as to be electrically connected with stripe electrodes on other planar insulating substrates, thereby forming a more three-dimensional electric field distribution. When ions are injected in the direction of an arrow E as shown, the ions will be guided and focused to the common angle by the electric field distribution and then leave from the smallest triangular cell electrode, and the ions may leave from the common corner 504 by e.g., an extraction lens in connection with or in direct connection with a next-stage apparatus such as an ion analyzing apparatus and then enter the next-stage apparatus in an F direction.

FIG. 4c shows ion trajectories obtained by computer simulation in the embodiment, which are observed from the perspective of the planar insulating substrate 501, and when viewed from a negative direction of a y axis as shown, diverging ion beams entering in the E direction are well focused by the apparatus and then leave from the common corner by e.g., an extraction lens.

It should be noted that the implementation of an ion focusing function is provided in the above embodiment, but those skilled in the art can fully perform a reverse operation according to the foregoing contents to achieve an ion defocusing function, for example, ions are reversely injected and a reversed DC voltage is applied, etc., which will not be described by way of example.

Two embodiments shown in FIGS. 5a and 5b below relate to the use of a geometric pattern distribution of an electrode array to realize periodic ion focusing or defocusing.

Figure 5A:
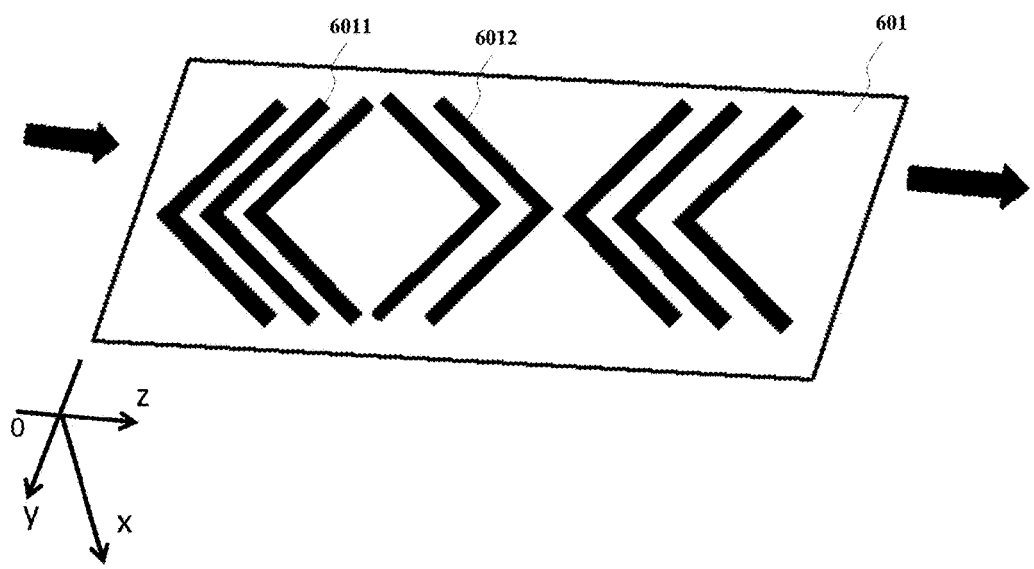
FIG. 5a shows a schematic structural view of an embodiment of the ion optical apparatus of the invention for implementing periodic focusing and defocusing.

As shown in FIG. 5a, yet another embodiment is provided. With reference to the above principle, in the embodiment, cell electrodes 6011 and 6012 are no longer arranged in the same direction, i.e., for example, two broken-line cell electrodes 6011 and 6012 are no longer opened towards the same direction, but part of the openings are oppositely arranged, such that ions can be focused and defocused in a switching or alternating manner.

Figure 5B:
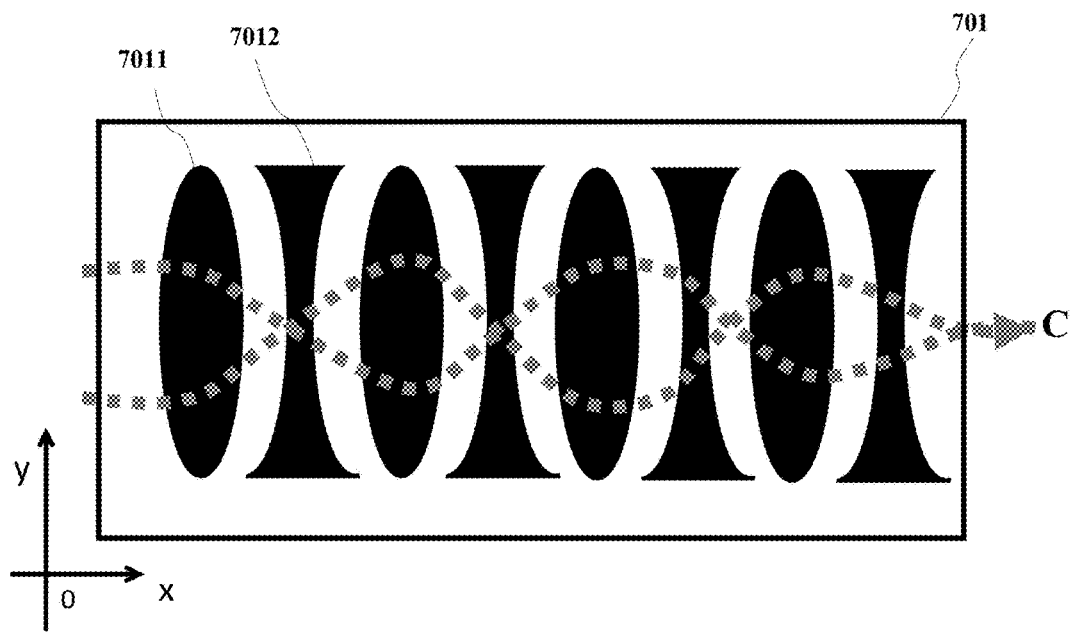
FIG. 5b shows a schematic structural view of an embodiment of the ion optical apparatus of the invention for implementing periodic focusing and defocusing.

Turn to FIG. 5b, which shows a more preferred arrangement of an electrode array for the periodic alternation of ion focusing and defocusing. In the embodiment, cell electrodes having more flexible and variable geometries are used in this manner to realize complex functions. Cell electrodes on a planar insulating substrate 701 are divided into concave electrodes 7012 and convex electrodes 7011, wherein the DC potential of the electrodes 7011 and 7012 gradually decreases in a positive direction of an x axis as shown. The concave electrodes 7012 and the convex electrodes 7011 in the array are staggered and hence can form a periodic focusing and defocusing electric field, such that ions are periodically focused and defocused during their transmission in the positive direction of the x axis as shown, thereby forming a trajectory C as shown. Such periodic electric field has many applications, for example, in a higher vacuum environment, the electric field can be used for adjusting the spatial phase distribution of ion beams to e.g., realize a function similar to that of an Einzel lens. Moreover, the periodic electric field can be used instead of an RF electric field to confine ions under a certain pressure, and can also serve as an ion migration tube in some embodiments.

Figure 6:
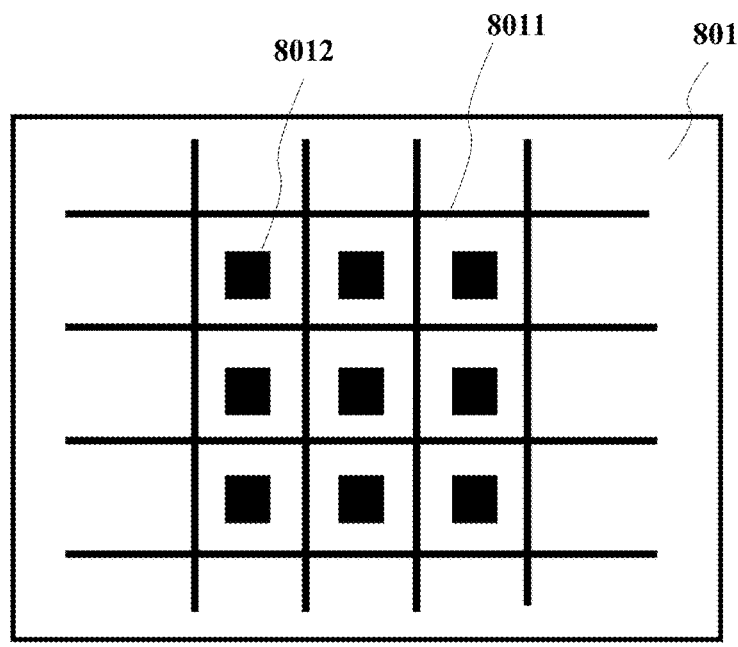
FIG. 6 shows a schematic structural view of an embodiment of the ion optical apparatus of the invention for implementing confinement to ion packets.

The geometric pattern distribution of the electrode array can also be used to form a bound ion packet. As shown in FIG. 6, in one embodiment, cell electrodes on a planar insulating substrate 801 may include grid electrodes 8011 and block electrodes 8012 in the grid electrodes, and a DC voltage bias is applied between the grid electrodes 8011 and the block electrodes 8012 (for example, the grid electrodes have a DC voltage higher than the block electrodes 8012) such that a DC potential barrier "pit" can be formed in each grid, then ions will be bound in individual pits after entering a position above the planar insulating substrate 801, and meanwhile RF voltages can be applied between the grid electrodes 8011 and the block electrodes 8012 to prevent the ions from striking on electrode surfaces. These isolated bound ion packets can be used to perform various forms of ion manipulation such as ion storage, coarse ion screening and ion reaction.

Figure 7A:
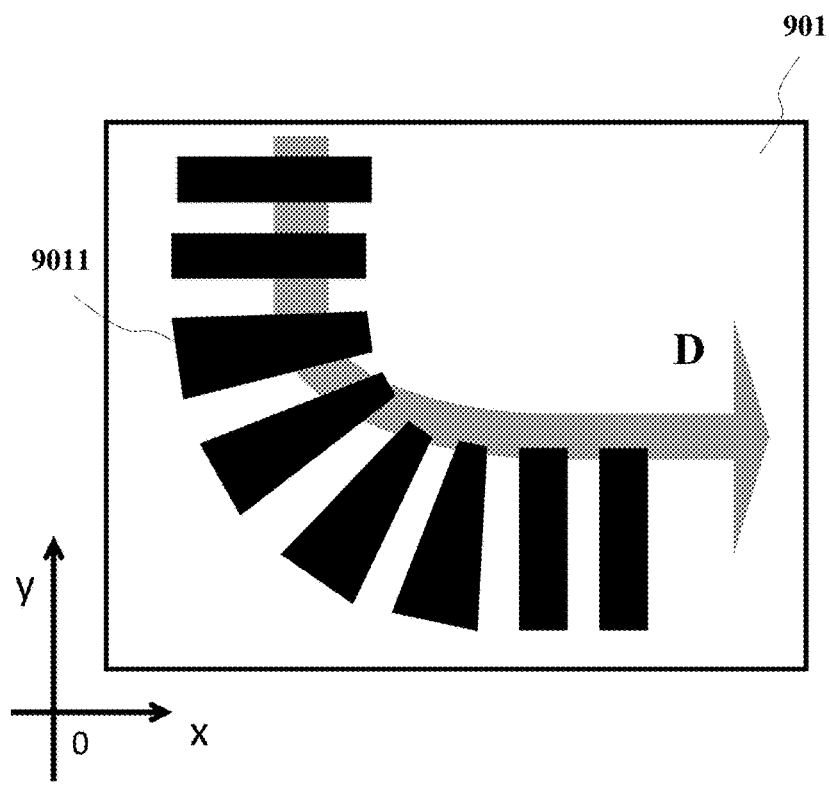
FIG. 7a shows a schematic structural view of an embodiment of the ion optical apparatus of the invention for implementing ion deflection.
Figure 7B:
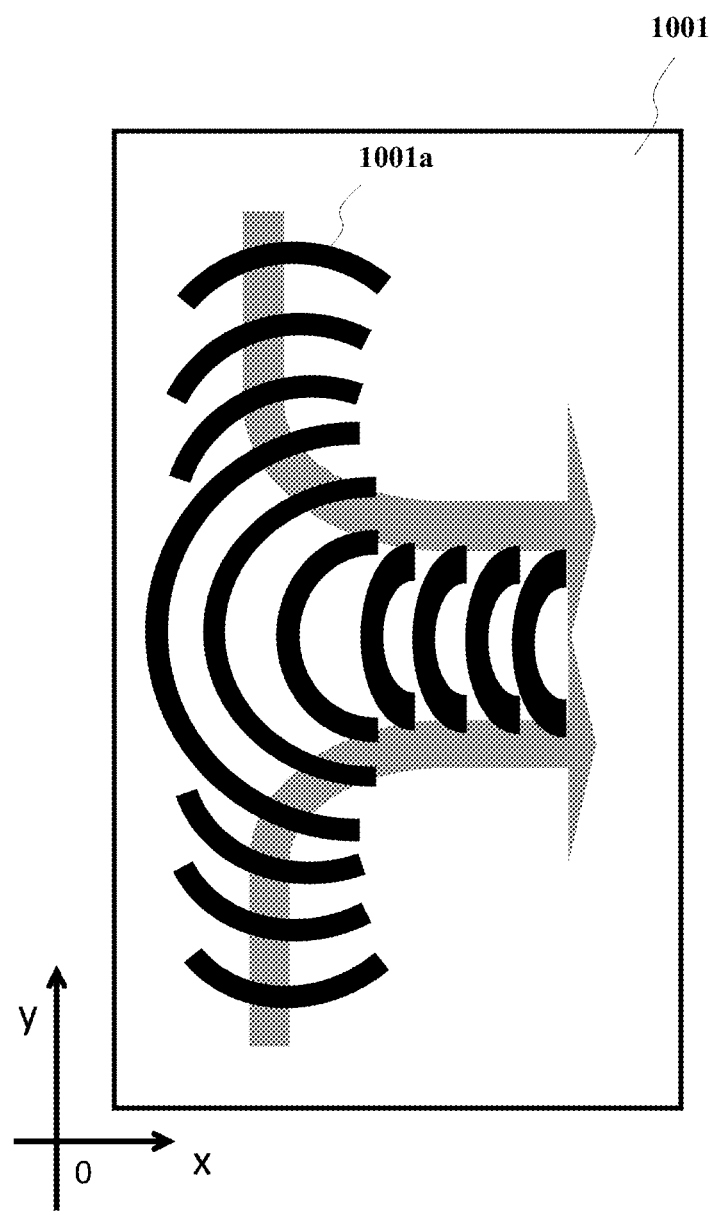
FIG. 7b shows a schematic structural view of an embodiment of the ion optical apparatus of the invention for implementing ion deflection.

Hereinafter, FIGS. 7a and 7b show the use of a geometric pattern distribution of an electrode array to realize the deflection of ions in a radial direction substantially orthogonal to an axial direction in which the ions move.

In one embodiment, as shown in FIG. 7a, the embodiment serves to illustrate an approach to realizing radial ion deflection, wherein the electrode array is distributed on a planar insulating substrate 901, the electrode array can be gradually distributed in a positive direction of an x axis and applied with a gradually decreasing DC potential so as to divert ion beams in a negative direction of a y axis to the positive direction of the x axis, and cell electrodes 9011 at a corner can be trapezoidal (as shown) to allow an electric field at the corner to be relatively uniform, thereby providing an ion moving trajectory shown as D. Radial ion deflection is widely used in a mass spectrometer, for example, such deflection can reduce neutral noise or instrument size, or can be used in a cycle structure to realize some special purposes.

In one embodiment, FIG. 7b shows how to converge and deflect two ion beams. The electrode array as shown just needs to be plated on a planar insulating substrate 1001, wherein the geometry of cell electrodes 1001a is an arc, and functions such as ion beam converging and deflection as shown can be formed by use of the arcuate radius or a gradual change radian or a gradual change in the direction of the arc. Ion reaction can be performed in a mass spectrometer in this manner, or analyzing throughput is improved by multi-path introduction.

In summary, parameters determining the geometric pattern distribution of the electrode array include one of the length, radius and curvature of the electrode array and an included angle relative to the predefined ion guiding direction, or one or more combinations thereof, and changes can be made by those skilled in the art in conjunction with the above embodiments and teachings provided in the invention as well as practical environments, but the above embodiments are not intended to be limiting.

A specific fabrication process, an improvement and some variation examples of the ion optical apparatus of the invention will be described below with reference to the embodiment in FIG. 2a.

Figure 8:
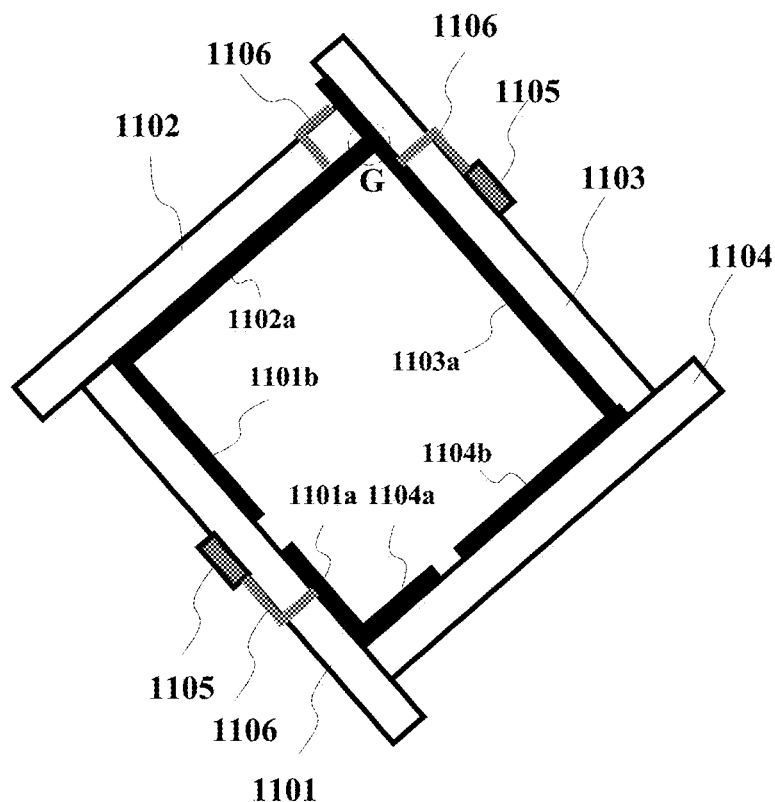
FIG. 8 shows a schematic structural view of a specific implementation of the embodiment of FIG. 2b.

FIG. 8 shows an embodiment corresponding to the specific implementation of FIG. 2b, wherein a planar insulating substrate and an electrode array thereon are fabricated by a printed circuit board (PCB) in the specific implementation. Four planar insulating substrates 1101, 1102, 1103 and 1104 may be of any material that can be used by a traditional PCB process, e.g., FR4, PTFE, ceramics, etc. Moreover, the electrode array is fabricated by printing a metal coating, and all traditional PCB processes such as metal deposition, electroplating, etching and resistance welding may be used in the fabrication process. In the following embodiment, the four planar insulating substrates (1101-1104), i.e., printed circuit boards, form a cuboid-shaped ion guiding chamber in a surrounding manner, and the metal coating is located on an inner surface of the chamber. The metal coating forms an upper first electrode array and a lower second electrode array which are combined to form an integral electrode array, the voltage applied on the electrode array is as described above, and electronic components 1105 (e.g., capacitors, resistors, etc.) that supply desired voltages to the electrode array are located outside the ion guiding chamber, and can be directly distributed at the other sides of the planar insulating substrates 1101 and 1103. Electronic components 1106 are electrically connected with electrodes via through holes on the planar insulating substrates by printed circuits. However, since cell electrodes on different planes, e.g. 1102a and 1103a, need to be electrically connected with each other, these cell electrodes may be directly connected by means of welding, but this manner might damage the electrode shape. In order to avoid damage, the electrode 1103a may be extended to a rear face of the substrate 1102 so as to be welded with a circuit 1106 pre-arranged at the rear face and then connected with the cell electrode 1102a via the through hole on the planar insulating substrate 1102.

Since the electrode array has a greater number of cell electrodes, there are also a greater number of welding spots, wherein a plurality of welding spots G (as shown) is provided corresponding to the number of the electrodes and distributed in a wiring manner in a direction parallel to an axial direction of the ion guiding chamber, thus the entire apparatus may have a certain stress to prevent deformation just by being connected via the welding spots. Indeed, a fixing device and a positioning device may also be added such that the ion transmission device is more secure and less prone to deformation. By use of such embodiment, the entire apparatus has lower cost and can be easily fabricated on a large scale, and because the electrodes are distributed on surfaces and have a very small thickness, the capacitance of the entire apparatus is also greatly reduced, and a high-power source is not required when RF voltages are applied.

Figure 9A:
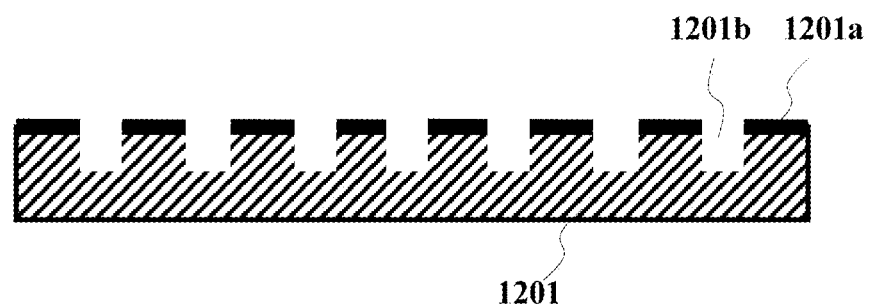
FIG. 9a shows a schematic structural view of an embodiment of the ion optical apparatus of the invention.

In addition, FIG. 9a shows a sectional view of an electrode with a three-dimensional structure formed by a micro/nanofabrication process. The specific discussion on the micro/nanofabrication process is beyond the scope of this patent. However, in general, the contents encompassed in the fabrication process are not limiting when applied to the ion optical apparatus of the invention. For example, as shown in FIG. 9a, an electrode coating 1201a and a planar insulating substrate 1201 can be formed by photolithography.

It should be noted that, in the above embodiment, intervals 1201a between the adjacent electrodes distributed in a spaced manner are insulating layers of the planar insulating substrate 1201, but electrostatic charges are easily accumulated on the insulating layers after electrodes are charged with RF voltages. Turn to FIG. 9a, wherein cut slots 1201b are arranged at spaced portions of the insulating layers, and can be formed by a dry process, wet etching and the like. The presence of the cut slots 1201b among the electrodes can effectively avoid the accumulation of the electrostatic charges on the insulating layers, because the presence of the RF voltages on the electrodes will inhibit the charges from entering deeper insulating cut slots 1201b. It is generally believed that the accumulation of electrostatic charges will adversely affect an ion optical device. To eliminate the accumulation of electrostatic charges, surface treatment may also be used in addition to the cut slots 1201b, for example, a high-resistance film is plated instead, and a layer of a dielectric material may also be coated around the electrodes.

It should be noted that these methods for eliminating electrostatic charges also apply to the fabrication of the ion optical apparatus of the invention by the above PCB process.

Figure 9B:
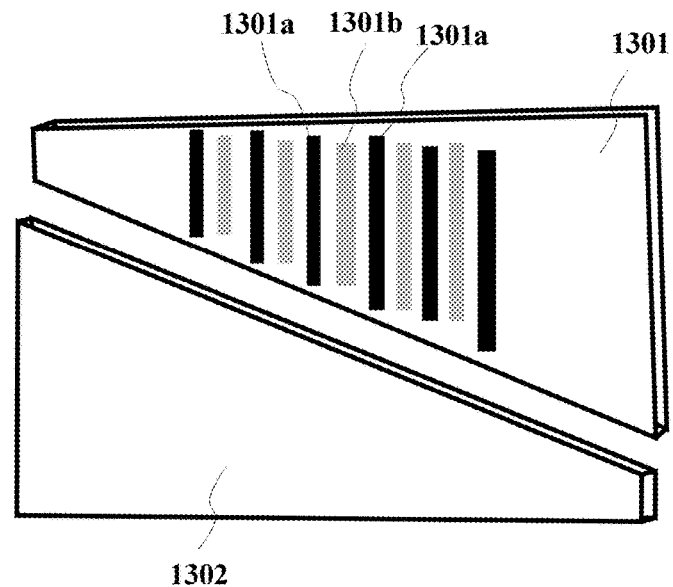
FIG. 9b shows a schematic structural view of an embodiment of the ion optical apparatus of the invention.

FIG. 9b shows another improvement of the embodiment. Compared with FIG. 2a, oblique insulating layers are omitted and discrete insulating substrates 1301 and 1302 are used instead in this embodiment, which has the advantage of increasing the permeability of the apparatus such that air flow in the apparatus is more uniform to avoid eddy flow, thereby facilitating ion transmission. Optionally, a plurality of channels 1301b may be segmented in any insulating portion (e.g. between electrodes 1301a) to form a more permeable structure.

Figure 10:
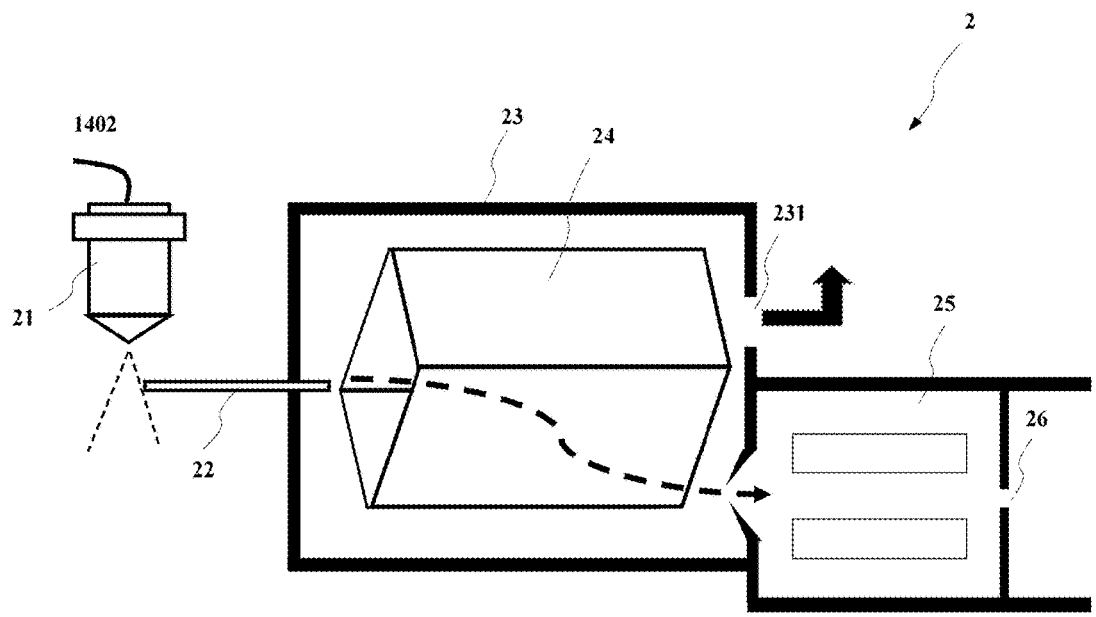
FIG. 10 shows a schematic structural view of an embodiment of a mass spectrometer used in the ion optical apparatus of the invention.

As shown in FIG. 10, the ion optical apparatus of the invention can be used as a preceding stage of a mass analyzer of a mass spectrometer 2 for ion guiding. Optionally, the ion analyzer can also comprise an ion mobility analyzer. In this embodiment, ions generated from an ion source 21 (e.g. an electrospray ion source, etc.) enter an ion optical apparatus 24 in a vacuum chamber 23 through a capillary tube 22 with a vacuum interface. In view of the properties of the ion optical apparatus 24 as previously described, ions move in an axial direction, then are transmitted radially in an off-axis manner and focused, and enter a next-stage apparatus 25 via a vacuum interface 231 for analysis. A suction port 232 is arranged in an axial direction of the ion optical apparatus 24 to suck out neutral components (mainly liquid droplets and gas with a solvent not fully removed) to reduce instrument noise. Accordingly, the ion optical apparatus 24 of the invention not only can focus ion beams to improve the signal intensity of ions, but also can reduce the noise interference from the previous stage, thereby improving instrument sensitivity. It should be noted that, compared with an stacked-ring structure in an ion funnel and the like, the array structures, in the form of a rectangle and a cuboid comprising rectangles, provided in the embodiments of the invention can provide a stronger RF potential barrier near an ion exit and therefore have a stronger confining effect on low-mass ions, thereby reducing the discrimination to low-mass ions in a mass spectrometer, the problem of which frequently makes those skilled in the art confused.

Figure 11A:
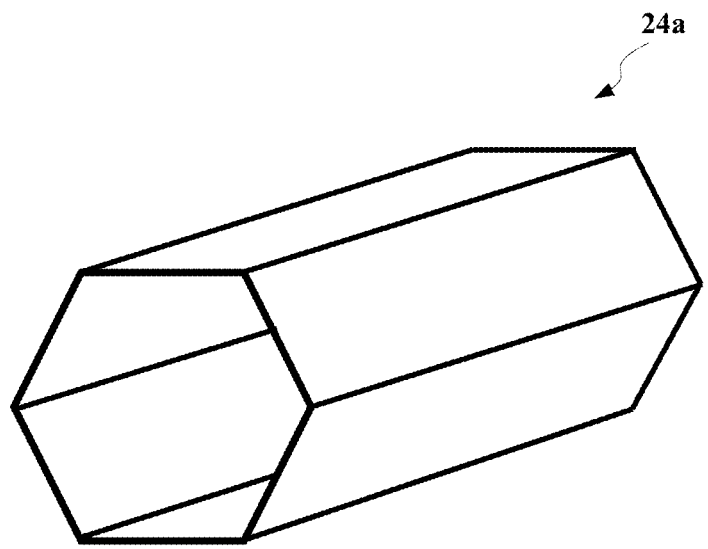
FIG. 11a shows a schematic structural view of an embodiment of an integral structure of the ion optical apparatus of the invention.
Figure 11B:
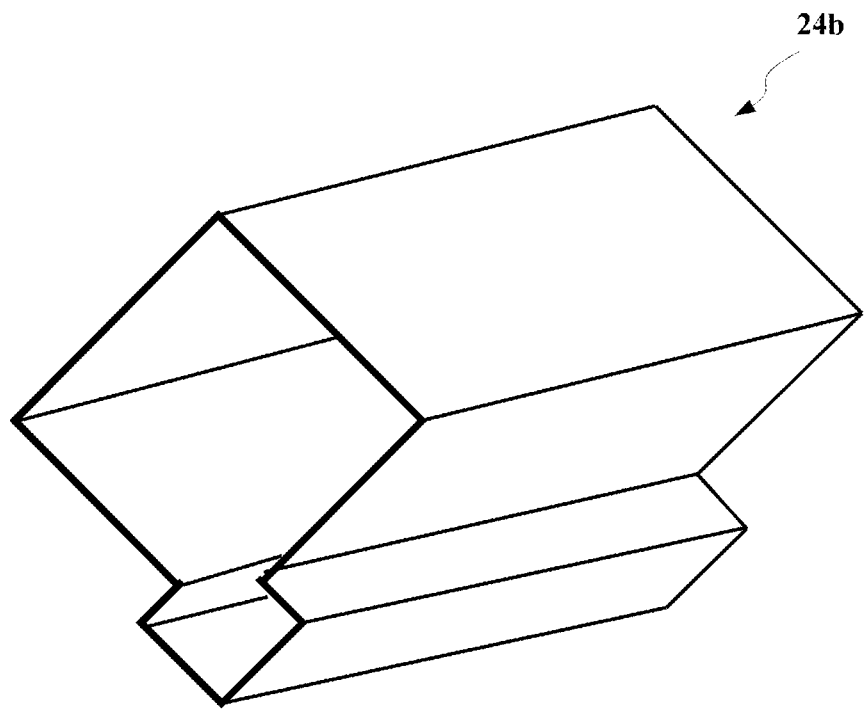
FIG. 11b shows a schematic structural view of an embodiment of an integral structure of the ion optical apparatus of the invention.

Indeed, the ion optical apparatus is not limited to the shape of the cuboid formed in a surrounding manner, with reference to FIGS. 11a and 11b. As shown in FIG. 11a, an ion optical apparatus 24a may be a structure including six substrates, wherein the section of an inlet is a centrosymmetric hexagon, the axial direction of the structure is the direction of a central axis of the hexagon, and the structure can generally be used in the case of an RF multi-stage field. The principle of FIG. 11b similar to that of the above FIG. 11a is used for off-axis transmission of ions, and the fabrication process can be greatly simplified by an ion optical apparatus 24b mentioned in the invention.

Optionally, in the above-mentioned embodiments, the joined edges of the planar insulating substrates which are joined in a surrounding manner to form an ion guiding chamber are parallel to axial lines in the invention, thereby forming an ion optical apparatus extending in an axial direction and radially focusing or deflecting ions. Compared with a non-parallel structure in the prior art, the apparatus in this patent is easier in machining, assembling and circuit connection.

In summary, the invention provides an ion optical apparatus and a mass spectrometer. The ion optical apparatus comprises at least one planar insulating substrate which is covered with metal patterns to form an electrode array comprising a plurality of cell electrodes, wherein the plurality of cell electrodes is arrayed according to a predefined ion guiding direction (i.e., a first direction) to form a geometric pattern distribution of the electrode array; each of adjacent and mutually insulated cell electrodes is applied with RF voltages having different phases to confine ions; a DC voltage gradient is also applied along at least part of the cell electrodes in the electrode array to drive ions to move in the first direction along the electrode array; and a corresponding electric field distribution is formed by the geometric pattern distribution, and the electric field distribution drives ions to move in a second direction substantially orthogonal to the first direction, thereby realizing ion deflection, focusing or defocusing. In the invention, various desired spatial electric field distributions are formed by the geometric structure and distribution of the planar electrodes. In one preferred embodiment, ions can be effectively focused within a broader pressure range by only two flat PCBs; and in another preferred embodiment, ions can be transmitted in an off-axis manner and focused to reduce neutral noise. In implementation, cell electrodes having various planar geometries are printed by a PCB or MEMS process, which provides the advantages of low cost, high precision, high flexibility, etc.

The above embodiments are only used for illustratively describing the principle and effects of the invention, but are not intended to limit the invention. Any persons skilled in the art can make modifications or changes to the above embodiments without departing from the spirit and scope of the invention. Accordingly, all equivalent modifications or changes made by the persons having ordinary skill in the art without departing from the spirit and technical ideas disclosed in the invention still shall be covered by the claims of the invention.

What is claimed is:

1. An ion optical apparatus, characterized by comprising:
at least one planar insulating substrate which is covered with metal patterns to form an electrode array, wherein the electrode array comprises a plurality of cell electrodes, the plurality of cell electrodes is arrayed according to a predefined ion guiding direction to form a geometric pattern distribution of said electrode array, and said predefined ion guiding direction is defined as a first direction,
wherein each of adjacent cell electrodes is applied with RF voltages having different phases to confine ions, a DC voltage gradient is also applied along at least part of the cell electrodes in the electrode array to drive ions to move in the first direction, and a corresponding electric field distribution is formed by the geometric pattern distribution of the electrode array and drives said ions to move in a second direction substantially orthogonal to the first direction, thereby realizing ion deflection, focusing or defocusing.

2. The ion optical apparatus according to claim 1, characterized in that at least part of the cell electrodes in the electrode array is in a broken line geometry or a curved line geometry to form an electric field distribution corresponding to the geometric pattern distribution of the electrode array.

3. The ion optical apparatus according to claim 1, characterized by comprising at least a pair of the planar insulating substrates which are arranged such that respective cell electrodes are opposite to each other in the second direction to form an electric field distribution between paired planar insulating substrates, thereby causing the ions to deflect, focus or defocus in the second direction.

4. The ion optical apparatus according to claim 1, characterized by comprising at least two said planar insulating substrates having a common edge formed by edge joining or at least three said planar insulating substrates having a common corner formed by corner joining, wherein said cell electrodes having gradually reduced sizes are distributed in a direction where the cell electrodes come closer to a point on the common edge or the common corner, such that the ions are focused towards the point on the common edge or the common corner.

5. The ion optical apparatus according to claim 1, characterized by comprising at least four said planar insulating substrates which are joined in a surrounding manner to form an ion guiding chamber, arrays of ring electrodes being formed in a spaced manner on an inner surface of the ion guiding chamber in the first direction, wherein at least part of the ring electrodes on at least two said planar insulating substrates are respectively isolated into two segments by an oblique insulating strip to form a first cell electrode and a second cell electrode such that the first cell electrode and the second cell electrode gradually change in length in the predefined ion guiding direction, and a DC voltage bias is applied between the first cell electrode and the second cell electrode so as to drive the ions to be focused while deflecting in the second direction.

6. The ion optical apparatus according to claim 1, characterized by comprising at least four said planar insulating substrates which are joined in a surrounding manner to form an ion guiding chamber, wherein a plurality of cell electrodes is arranged in a spaced manner on each surface inside the ion guiding chamber in the first direction and the second direction, and different DC voltages are applied along at least part of the cell electrodes to form a corresponding electric field distribution so as to drive the ions to deflect, focus or defocus in the second direction.

7. The ion optical apparatus according to claim 6, characterized in that said DC electric field can be replaced by an RF electric field which generates pseudo potential barriers having different intensities in the second direction to drive the ions to deflect, focus or defocus.

8. The ion optical apparatus according to claim 1, characterized in that parameters involving the geometric pattern distribution of the electrode array include one of the length, radius and curvature of the cell electrodes in the electrode array and an included angle relative to the first direction, or one or more combinations thereof.

9. The ion optical apparatus according to claim 8, characterized in that the parameters gradually change in the first direction to form a corresponding electric field distribution.

10. The ion optical apparatus according to claim 1, characterized in that the planar insulating substrate is in a rectangular shape.

11. The ion optical apparatus according to claim 1, characterized in that the planar insulating substrate is a substrate of a printed circuit board and the metal pattern is a printed circuit.

12. The ion optical apparatus according to claim 1, characterized in that the at least part of electronic components for forming the DC or RF electric field are located on the printed circuit board.

13. The ion optical apparatus according to claim 1, characterized in that a portion of the planar insulating substrate that is not covered with the metal patterns is provided with a cut slot or covered with a coating having a high resistance value.

14. The ion optical apparatus according to claim 1, characterized in that the planar insulating substrate and the metal patterns are obtained by a micro/nanofabrication process.

15. A mass spectrometer, characterized by comprising the ion optical apparatus according to claim 1 for ion guiding.

16. The mass spectrometer according to claim 15, characterized by comprising a mass analyzer used in combination with the ion optical apparatus.

17. The mass spectrometer according to claim 15, characterized by comprising an ion mobility analyzer used in combination with the ion optical apparatus.

* * * * *